United States Patent [19]
Seckinger et al.

[11] 3,966,805
[45] June 29, 1976

[54] N,N'-DIPHENYL-N-(N''-ALKYLCAR-
BAMOYL)FORMAMIDINES

[75] Inventors: Karl Seckinger, Riegel, Germany;
Fritz Reisser, Therwil, Switzerland

[73] Assignee: Sandoz Ltd., Basel, Switzerland

[22] Filed: Feb. 23, 1973

[21] Appl. No.: 335,050

[30] Foreign Application Priority Data
Feb. 29, 1972  Switzerland............... 2859/72

[52] U.S. Cl............... 260/553 A; 71/120; 71/103
[51] Int. Cl.² ............ C07C 127/19; A01N 9/20
[58] Field of Search ................. 260/553 A

[56] References Cited
UNITED STATES PATENTS
3,242,209  3/1966  Jentzsch et al............. 260/553 R X
3,340,254  9/1967  Jentzsch et al............. 260/553 A X
3,898,277  8/1975  Duerr et al................ 260/553 A

*Primary Examiner*—James O. Thomas, Jr.
*Assistant Examiner*—G. Breitenstein
*Attorney, Agent, or Firm*—Gerald D. Sharkin; Richard E. Vila

[57] ABSTRACT

The present invention concerns novel N,N'-diphenyl-N-(N''-alkylcarbamoyl)formamidine derivatives of the formula:

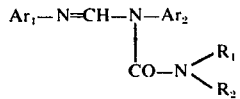

wherein $R_1$ is hydrogen or alkyl, $R_2$ is alkyl and $Ar_1$ and $Ar_2$ are each phenyl or a substituted phenyl, which compounds are useful as herbicides.

37 Claims, No Drawings

N,N'-DIPHENYL-N-(N''-ALKYLCARBAMOYL)-FORMAMIDINES

The present invention relates to N,N'-diphenyl-N-(N''-alkylcarbamoyl)formamidine derivatives.

The present invention provides compounds of formula I,

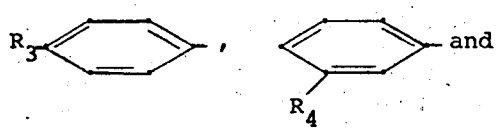

wherein
$R_1$ is hydrogen or alkyl of 1 to 4 carbon atoms,
$R_2$ is alkyl of 1 to 4 carbon atoms, and either
$Ar_1$ and $Ar_2$ are the same, and are each phenyl or a substituted phenyl group selected from

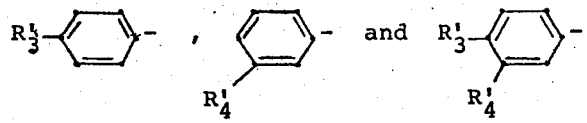

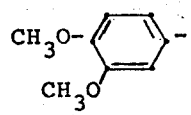

wherein
$R_3$ is chlorine, bromine, methyl, methoxy, or dimethyl or diethylsulphonamide and
$R_4$ is chlorine, bromine, methyl, methoxy or trifluoromethyl, or
$Ar_2$ is phenyl and
$Ar_1$ is a substituted phenyl group selected from

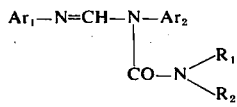

wherein
$R_3'$ is chlorine or methyl and
$R_4'$ is chlorine, methyl or trifluoromethyl,
with the proviso that $Ar_1$ and $Ar_2$ are other than

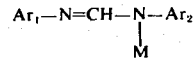

When $R_1$ or $R_2$ is alkyl, this is preferably of 1 to 3 carbon atoms, e.g. methyl, ethyl, n-propyl or i-propyl, and more preferably is methyl.

The present invention also provides a process for the production of a compound of formula I which comprises
a. reacting a compound of formula IIa $$Ar_1-N=CH-N-Ar_2$$
$$|$$
$$M$$

IIa wherein $Ar_1$ and $Ar_2$ are as defined above and
M is a salt forming atom or group, preferably an alkali metal, especially sodium,
with a compound of formula III,

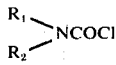

III wherein $R_1$ and $R_2$ are as defined above, or
b. reacting a compound of formula IIb,

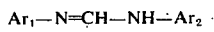

IIb wherein $Ar_1$ and $Ar_2$ are as-defined above, with a compound of formula IV,

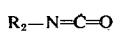

IV wherein $R_2$ is as defined above, to product a compound of formula Ia,

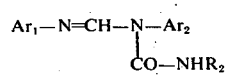

wherein $Ar_1$, $Ar_2$ and $R_2$ are as defined above.

The process of the invention, in accordance with variant (a) above, may be effected as follows:

A compound of formula IIa may be dissolved or suspended in an inert solvent or suspension medium and a compound of formula III, which may also be dissolved or suspended in an inert solvent or suspension medium, added thereto. Examples of suitable solvents or suspension media are hexamethyl phosphoric triamide or benzene. The reaction may conveniently be effected at room temperature, preferably over a prolonged period e.g. 12 hours, and conveniently with stirring. Working up may be effected in conventional manner.

In a preferred modification of the process variant described above, the compound of formula IIa is produced in situ and without isolation, from a compound of formula IIb, by reaction with a strong base, e.g. sodium hydride. The process may be effected by adding a compound of formula III, which may be dissolved or suspended in a suitable solvent or suspension medium to a mixture of a compound of formula IIb and a strong base, in an inert solvent or suspension medium. Examples of suitable solvents or suspension media are hexamethyl phosphoric triamide or benzene. The reaction may then be effected as described above. With respect to the working up of the reaction mixture, excess of the strong base, e.g. sodium hydride, is carefully decomposed, for example, by the addition of water while cooling with ice. In the case where a water immiscible solvent or suspension medium is employed, addition of water may be continued until well separated phases have been obtained. Further working up may be effected in conventional manner.

The process of the invention in accordance with variant (b) above, may be effected as follows:

A compound of formula IV is added to a compound of formula IIb in an inert solvent, such as absolute toluene, and the mixture is reacted at an elevated temperature, e.g. 80°C, and at an elevated pressure. The mixture may be allowed to react over a prolonged period, e.g. 60 hours. The reaction is preferably effected in an autoclave. Working up is effected in conventional manner.

The compounds of formula I are, in general, colourless crystalline substances. Purification may be effected by recrystallisation from suitable solvents, e.g. ethyl acetate or an ethyl acetate/hexane mixture.

The compounds of formula IIa, employed as starting material in process variant (a), may be obtained as described above, from a compound of formula IIb, by reaction with a strong base, e.g. sodium hydride.

The compounds of formula IIb, employed as starting material in process variant (b), and also in the production of a compound of formula IIa, may be obtained in manner known per se, a' by reacting a compound of formula V

    V wherein
Ar$_1$ is as defined above and
R$_5$ is alkyl of 1 to 4 carbon atoms, preferably ethyl, with a compound of formula VI,

    VI wherein Ar$_2$ is as defined above, or b' by reacting two equivalents of a compound of formula VI with one equivalent of a compound of formula VII,

    VII wherein
R$_6$ is alkyl is 1 to 3 carbon atoms, preferably ethyl, to produce a compound of formula IIb'

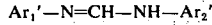    IIb' wherein Ar$_1$' and Ar$_2$' have the same significances as Ar$_1$ and Ar$_2$ respectively, defined above, with the proviso that Ar$_1$' is the same as Ar$_2$'.

The compounds of formulae III, IV, V, VI and VIII are either known or, insofar as they are not known, they may be produced in analogous manner to the processes for the production of the known compounds.

The compounds of formula I are useful because they possess biological activity in plants. In particular the compounds of formula I are useful as herbicidal agents, as indicated in the following test viz:

Test 1

The compounds were applied to cultures of the weed species
 Amaranthus retroflexus,
 Capsella bursa pastoris,
 Chenopodium album,
 Galium aparine,
 Stellaria media,
 Senecio vulgaris,
 Echinochloa crus-galli,
 Alopecurus myosuroides
 and Agrostis alba
post emergence, at concentrations of 2½ and 3 kg/hectare. The cultures were examined 14 days after application. A significant herbicidal effect was observed against each of the weeds at the concentrations tested.

In addition, the compounds of formula Ib,

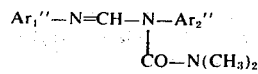    Ib wherein Ar$_1$'' and Ar$_2$'' are the same and are each a substituted phenyl group selected from

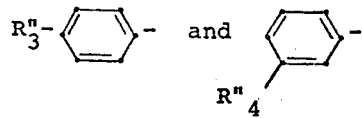

wherein R$_3$'' and R$_4$'' are each chlorine, bromine or methyl, and the compounds of formula Ic,

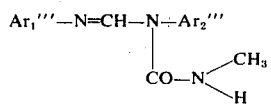    Ic wherein Ar$_1$''' and Ar$_2$''' are the same and are each a substituted phenyl group selected from

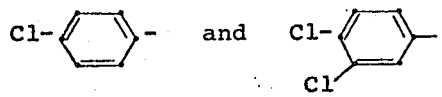

are further useful as selective herbicidal agents in combating weeds in cotton and potato cultures respectively, as indicated by the following tests:

Test 2

In the case of the compounds N,N'-di-(4-chlorophenyl)-N-(N''-methylcarbamoyl)-formamidine and N,N'-di-(3,4-dichlorophenyl)-N-(N''-methylcarbamoyl)-formamidine, Test 1 was conducted in a potato culture containing the abovementioned weeds, post emergence, at a concentration of 3 kg/hectare of the compounds. No significant effect on the potatoes was observed at the concentration tested whereas a significant effect was observed against the weeds.

Test 3

Compounds of formula Ib, were tested in cotton cultures (Gossypium hirsutum) containing the following weeds species
 Sida spinosa,
 Echinochloa crus galli,
 Amaranthus retroflexus,
 Ipomoea rubra,
 Digitaria sanguinalis,
 Chenopodium album,
 Sisymbrium irio
 and Postulaca oleracea.

The compounds were applied at a concentration of 3 kg/hectare pre-emergence and 2½ kg/hectare post emergence. In both cases, a significant herbicidal effect against the weed species was observed with no significant effect on the cotton crop.

The preferred compounds of formula I are the compounds of formulae Ib and Ic. Particularly interesting compounds of formula Ib are the compounds
 N-N'-di-(3-chlorophenyl)-N-(N''-dimethylcarbamoyl)-formamidine, N,N'-di-(4-chlorophenyl)-N-(N''-dimethylcarbamoyl)-formamidine,
N,N'-di-(4-bromophenyl)-N-(N''-dimethylcarbamoyl)-formamidine,
N,N'-di-(3-methylphenyl)-N-(N''-dimethylcarbamoyl)-formamidine and
N,N'-di-(4-methylphenyl)-N-(N''-dimethylcarbamoyl)-formamidine.

However, other groups of compounds falling within the scope of formula I may also be mentioned as having interesting properties, e.g. the compounds of formula Id,

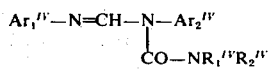

wherein
$R_1^{IV}$ is alkyl of 1 to 4 carbon atoms,
$R_2^{IV}$ is alkyl of 1 to 4 carbon atoms and
$Ar_1^{IV}$ and $Ar_2^{IV}$ are the same and are each phenyl or a substituted phenyl group selected from

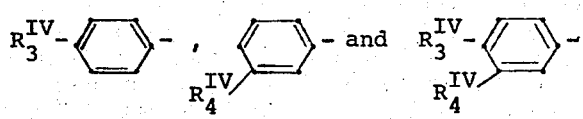

wherein
$R_3^{IV}$ is chlorine, methoxy or diethylsulphonamide and
$R_4^{IV}$ is chlorine, methoxy or trifluoromethyl
with the proviso that $Ar_1^{IV}$ and $Ar_2^{IV}$ are other than

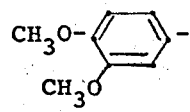

and the compounds of formula Ie,

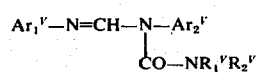

wherein
$R_1^V$ is alkyl of 1 to 4 carbon atoms,
$R_2^V$ is alkyl of 1 to 4 carbon atoms,
$Ar_2^V$ is phenyl and
$Ar_1^V$ is a substituted phenyl group selected from

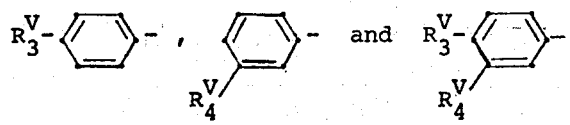

wherein
$R_3^V$ is chlorine or methyl and
$R_4^V$ is chlorine or methyl.

For the abovementioned uses, the amount of compound to be applied to a weed infested locus will vary depending on the particular compound employed, mode of application, ambient conditions, the weeds species to be combated and the cultivated crop, if any, involved. However, in general, a suitable amount to be applied to a locus is between 1 and 10 kg/hectare of the compound, the application to be repeated as required.

The compounds may be employed as herbicidal compositions in association with herbicide carriers or diluents. Such compositions also form part of the present invention.

Herbicidal compositions may be employed in either solid or liquid application forms. Solid forms, e.g. dusting forms and granulates, may be produced by mixing or impregnating solid herbicide carriers such as diatomaceous earth, kaolin, talc, chalk, limestone and cellulose powder, with the compounds.

Additives may be employed in the herbicidal composition. Typical of such additives are wetting and dispersing agents, e.g. the condensation product of formaldehyde with naphthalene sulphonate, and alkyl benzene sulphonates, adhesion imparting agents, e.g. dextrin, and emulsion stabilizers, e.g. ammonium caseinate. Such additives are suitable for incorporation into, e.g. a wettable powder form of composition.

The herbicidal compositions may contain, aside from a compound of formula I as active agent, other active agents, such as herbicides, e.g. of the urea class, halogen benzonitriles, carbamates and triazines.

Concentrate forms of composition generally contain between 2 and 80%, preferably between 2 and 50%, by weight of a compound of formula I as active agent.

Application forms of composition generally contain between 0.01 and 10%, by weight of a compound of formula I as active agent.

Specific Examples of herbicidal compositions will now be described.

Example A

Wettable powder form of composition 25 parts of N,N'-di-(4-chlorophenyl)-N-(N''-dimethylcarbamoyl)formamidine, 5parts of a condensation product from formaldehyde and naphthalene sulphonate, 2 parts of alkyl benzene sulphonate, 5 parts of dextrin, 1 part of ammonium caseinate and 62 parts of diatomaceous earth are mixed until a homogeneous mixture is obtained and then ground until the particles are considerably smaller than 45 microns as an average.

Example B

Wettable powder form of composition 25 parts of N,N'-di-(4-chlorophenyl)-N-(N''-methylcarbamoyl)formamidine, 5 parts of a condensation product from formaldehyde and naphthalene sulphonate, 2 parts of alkyl benzene sulphonate, 5 parts of dextrin, 1 part of ammonium caseinate and 62 parts of diatomaceous earth are mixed until a homogeneous mixture is obtained and then ground until the particles are considerably smaller than 45 microns as an average.

Another aspect of the present invention provides a method of combating weeds in a locus, which comprises applying to the locus a compound of formula I.

the application of the compound may either be pre- or post-emergence of the weeds, and where the locus is a cultivated crop locus and the method is for the selective combating of weeds in the cultivated crop, the compound may be applied either pre- or post-emergence of either the weeds or the crop. Preferably, the compound is applied post-emergence of the crop. The compound may be applied in the form of a herbicidal composition as has been described above.

Specific Examples illustrating the production of compounds of formula I will now be described. Where temperature is referred to, this is in degrees Centigrade.

EXAMPLE 1

N,N'-DI-(4-bromophenyl)-N-(N''-dimethylcarbamoyl)-formamidine (process a)

A solution of 35.4 g (0.1 mol) of N,N'-di-(4-bromophenyl) formamidine in 150 cc of hexamethyl phosphoric triamide is added dropwise, at room temperature, to a well stirred suspension of 3.1 g (0.13 mol) of sodium hydride in 100 cc of hexamethyl phosphoric triamide. The mixture is then stirred at room temperature over the course of 2 further hours; subsequently 10.7 (0.1 mol) of dimethylcarbamoyl chloride in 100 cc of hexamethyl phosphoric triamide are added dropwise and the mixture is stirred at room temperature over the course of 12 hours and then cooled in ice. The excess sodium hydride is initially carefully decomposed with a small quantity of water and a total of 2000 cc of water is subsequently added to the reaction mixture, which is extracted twice with 500 cc amounts of benzene. The benzene extracts are dried with potassium carbonate and evaporated. Colourless crystals with a M.P. of 121° are obtained from ether.

Analysis: $C_{16}H_{15}Br_2N_3O$: Molecular weight: 425.1
Calc. C, 45.2%; H, 3.6%; N, 9.9%; Br 37.6%.
Found: C, 45.7%; H, 3.9%; N, 10.1%; Br, 37.6%.

EXAMPLE 2

100 cc of absolute benzene. The suspension of the resulting sodium salt is subsequently stirred at room temperature over the course of 2 hours. 10.7 g (0.1 mol) of dimethylcarbamoyl chloride in 100 cc of absolute benzene are then added dropwise, the mixture is stirred at room temperature for 12 hours and cooled in ice. The excess of sodium hydride is carefully decomposed with a small quantity of water and a total of 300 cc of water is then added to the reaction mixture. The benzene phase is separated, dried with potassium carbonate and evaporated. Colourless crystals with a M.P. of 111°–112° are obtained from ether.

Analysis: $C_{16}H_{15}Cl_2N_3O$: Molecular weight: 336.2
Calc. C, 57.6%; H, 4.5%; N, 12.5%; Cl, 21.1%
Found: C, 57.3%; H, 4.6%; N, 12.1%; Cl, 20.7%.

EXAMPLE 3

N,N'-Di-(4-chlorophenyl)-N-N''-methylcarbamoyl)-formamidine (process b)

A mixture of 26.5 g (0.1 mol) of N,N'-di-(4-chlorophenyl) formamidine and 11.4 g (0.2 mol) of methyl isocyanate in 150 cc of absolute benzene is heated in a pressure autoclave up to 80° over the course of 60 hours. The autoclave is cooled and opened and the reaction solution is then evaporated down in a rotatory evaporator. The precipitated crystals are suction filtered and washed with petroleum ether. Colourless crystals with a M.P. of 134°–135° are obtained.

Analysis: $C_{15}H_{13}Cl_2N_3O$: Molecular weight: 322.2
Calc.: C, 55.9%; H, 4.1%; N, 13.0%; Cl, 22.0%.
Found: C, 56.3%; H, 4.1% N, 12.6% Cl, 21.8%.

The compounds of formula I of Examples 4 to 17 are obtained in analogous manner to that described in Examples 1 and 2:

| Example | | Empirical formula | Molecular weight | M.P. °C | ANALYSIS % Calc. Found | | | | | |
|---|---|---|---|---|---|---|---|---|---|---|
| | | | | | C | H | N | Cl | Br | F |
| 4 | N,N'-Diphenyl-N-(N''-dimethyl-carbamoyl)formamidine | $C_{16}H_{17}N_3O$ | 267.3 | 100 | 71.9 72.5 | 6.4 6.8 | 15.7 15.7 | | | |
| 5 | N,N'-Di-(4-chlorophenyl)-N-(N''-dimethylarbamoyl)for mamidine | $C_{16}H_{15}Cl_2N_3O$ | 336.2 | 124 | 57.2 57.2 | 4.5 4.4 | 12.5 12.4 | 21.1 21.1 | | |
| 6 | N,N'-Di-(3,4-dichlorophenyl)-N-(N''-dimethylcarbamoyl)-formamidine | $C_{16}H_{13}Cl_4N_3O$ | 405.1 | 165 | 47.5 47.7 | 3.2 3.2 | 10.4 10.0 | 35.0 34.9 | | |
| 7 | N,N'-Di-(3-trifluoromethyl-phenyl)-N-(N''-dimethylcarba-moyl)formamidine | $C_{18}H_{15}F_6N_3O$ | 403.3 | syrup | 53.7 53.4 | 4.5 3.8 | 10.4 10.9 | | | 28.2 28.3 |
| 8 | N,N'-Di-(4-methylphenyl)-N-(N''-dimethylcarbamoyl)-formamidine | $C_{18}H_{21}N_3O$ | 295.4 | 128–31 | 73.2 72.7 | 7.2 7.1 | 14.2 13.8 | | | |
| 9 | N,N'-Di-(4-bromophenyl)-N-(N''-dimethylcarbamoyl)-formamidine | $C_{16}H_{15}Br_2N_3O$ | 425.1 | 121 | 45.2 45.7 | 3.6 3.9 | 9.9 10.1 | | 37.6 37.6 | |
| 10 | N,N''-Di-(3-methoxyphenyl)-N,(N''-dimethylcarbamoyl)-formamidine | $C_{18}H_{21}N_3O_3$ | 327.4 | 98 | 66.0 66.2 | 6.5 6.6 | 12.8 13.2 | | | |
| 11 | N,N'-Di-(3-methylphenyl)-N-(N''-dimethylcarbamoyl)-formamidine | $C_{18}H_{21}N_3O$ | 295.4 | 57–58 | 73.2 73.2 | 7.2 7.1 | 14.2 14.4 | | | |
| 12 | N,N'-Di-(3-chloro-4-metoxyphenyl)-N-(N''-dimethylcarbamoyl)-formamidine | $C_{18}H_{19}Cl_2N_3O_3$ | 396.3 | 113 | 54.6 54.2 | 4.8 4.9 | 10.6 10.4 | 17.9 17.8 | | |
| 13 | N,N'-Di-(4-diethylsulfonamido-phenyl)-N-(N''-dimethylcarbamoyl)-formamidine | $C_{20}H_{27}N_5O_5S_2$ | 481.6 | 129–30 | 49.9 49.9 | 5.7 5.6 | 14.5 14.2 | | | |

N,N'-Di-(3-chlorophenyl)-N-(N''-dimethylcarbamoyl)formamidine (process a)

A solution of 26.5 g (0.1 mol) of N,N'-di-(3chlorophenyl)formamidine in 600 cc of absolute benzene is added dropwise at room temperature to a well stirred suspension of 3.1 g (0.12 mol) of sodium hydride in In like manner to the production of the compound of Example 13, the compound N,N'-di-(4-dimethylsulphonamidophenyl)-N-(N''-dimethylcarbamoyl)-formamidine is produced.

EXAMPLE 14

N-Phenyl-N-(N''-dimethylcarbamoyl)-N'-(3,4-dichlorophenyl)formamidine

M.P.: 126°–127°
Analysis: $C_{16}H_{15}Cl_2N_3O$: Molecular weight: 336.2:
Calc.: C, 57.1%; H, 4.5%; N, 12.5%; Cl, 20.9%.
Found: C, 56.7%; H, 4.5%; N, 12.8%; Cl, 21.5%.

EXAMPLE 15

N-Phenyl-N-(N''-dimethylcarbamoyl)-N'-(3,4-dimethylphenyl)formamidine

M.P.: 119°–120°
Analysis: $C_{18}H_{21}N_3O$: Molecular weight: 295.4:
Calc.: C, 73.2%; H, 7.2%; N, 14.2%.
Found: C, 73.5%; H, 7.2%; N, 14.2%.

EXAMPLE 16

N-Phenyl-N-(N''-dimethylcarbamoyl)-N'-(4-chlorophenyl)formamidine

M.P.: 112°–115°
Analysis: $C_{16}H_{16}ClN_3O$: Molecular weight: 301.8:
Calc.: C, 63.6%; H, 5.4%; N, 13.9%; Cl, 11.8%.
Found: C, 63.2%; H, 5.3%; N, 13.8%; Cl, 12.8%.

EXAMPLE 17

N-Phenyl-N-(N''-dimethylcarbamoyl)-N'-(4-methylphenyl)formamidine

M.P.: 74°–75°
Analysis: $C_{17}H_{19}N_3O$: Molecular weight: 281.4:
Calc.: C, 72.6%; H, 6.8%; N, 14.9%.
Found: C, 72.2%; H, 6.9%; N, 14.4%.

The compounds of formula I of Examples 18 to 33 may be produced in manner analogous to that described in Examples 1, 2 and 3:

EXAMPLE 29

N-Phenyl-N-(N''-methylcarbamoyl)-N'-(4-methylphenyl)formamidine

M.P.: 122°–124°
Analysis: $C_{16}H_{17}N_3O$: Molecular weight: 267,3:
Calc.: C, 71.9%; H, 6.4%; N, 15.7% Found: C, 71.7%; H, 6.4%; N, 15.6%.

EXAMPLE 30

N-Phenyl-N-(N''-methylcarbamoyl)-N'-(4-chlorophenyl)formamidine

M.P.: 120°–121°
Analysis: $C_{15}H_{13}ClN_3O$: Molecular weight: 286.7:
Calc.: C, 62.9%; H, 4.6%; N, 14.7%; Cl, 12.4%. Found: C, 62.6%; H, 4.9%; N, 14.2%; Cl, 11.2%.

EXAMPLE 31

N-Phenyl-N-(N''-methylcarbamoyl)-N'-(3,4-dimethylphenyl)formamidine

M.P.: 97°–102°
Analysis: $C_{17}H_{19}N_3O$: Molecular weight: 281.3:
Calc.: C, 72.7%; H, 6.8%; N, 14.9%. Found: C, 71.5%; H, 6.9%; N, 15.6%.

EXAMPLE 32

N-Phenyl-N-(N''-methylcarbamoyl)-N'-(3,4-dichlorophenyl)formamidine

M.P.: 107°–111°
Analysis: $C_{15}H_{13}Cl_2N_3O$: Molecular weight: 322.2.
Calc.: C, 56.0% ; H, 4.1% ; N, 13.0% ; Cl, 22.0% .
Found: C, 55.7%; H, 4.1%; N, 13.4%; Cl, 22.0%.

EXAMPLE

N-Phenyl-N-(N''-methylcarbamoyl)-N'-(3-trifluoromethylphenyl)formamidine

| Example | Empirical formula | Molecular weight | M.P. °C | ANALYSIS % Calc. / Found | | | | | |
|---|---|---|---|---|---|---|---|---|---|
| | | | | C | H | N | Cl | F | Br |
| 18 | N,N'-Diphenyl-N-(N''-methylcarbamoyl)formamidine | $C_{15}H_{15}N_3O$ | 253.1 | 158–59 | 71.1 / 71.3 | 6.0 / 5.9 | 16.6 / 16.8 | | | |
| 19 | N,N''-Di-(3,4-dichlorophenyl)-N-(N''-methylcarbamoyl)formamidine | $C_{15}H_{11}Cl_4N_3O$ | 391.1 | syrup | 46.0 / 47.2 | 2.8 / 3.4 | 10.7 / 10.7 | 36.1 / 35.7 | | |
| 20 | N,N'-Di-(3-bromophenyl)-N-(N''-methylcarbamoyl)formamidine | $C_{15}H_{13}Br_2N_3O$ | 411.1 | 100 | 43.8 / 44.1 | 3.2 / 3.2 | 10.2 / 10.1 | | | 38.9 / 38.5 |
| 21 | N,N'-Di-(3-trifluoromethylphenyl)-N-(N''-methylcarbamoyl)formamidine | $C_{13}H_{13}F_6N_3O$ | 389.3 | syrup | 52.4 / 53.1 | 3.4 / 3.4 | 10.8 / 10.4 | | 29.3 / 29.8 | |
| 22 | N,N'-Di-(4-bromophenyl)-N-(N''-methylcarbamoyl)-formamidine | $C_{15}H_{13}Br_2N_3O$ | 411.1 | 113–16 | 43.8 / 44.6 | 3.2 / 3.3 | 10.2 / 11.2 | | | 38.9 / 37.6 |
| 23 | N,N'-Di-(3-chloro-4-methylphenyl)-N-(N''-methylcarbamoyl)formamidine | $C_{17}H_{17}Cl_2N_3O$ | 350.2 | Sirup | 58.4 / 59.6 | 4.9 / 5.0 | 12.0 / 11.6 | 20.2 / 19.4 | | |
| 24 | N,N'-Di-(3-chlorophenyl)-N-(N''-methylcarbamoyl)-formamidine | $C_{15}H_{13}Cl_2N_3O$ | 322.2 | 100–101 | 55.9 / 56.4 | 4.1 / 4.0 | 13.0 / 13.1 | 22.0 / 21.7 | | |
| 25 | N,N'-Di-(4-methylphenyl)-N-(N''-methylcarbamoyl)-formamidine | $C_{17}H_{19}N_3O$ | 281.3 | 129–30 | 72.7 / 72.6 | 6.8 / 6.8 | 14.9 / 14.8 | | | |
| 26 | N,N'-Di-(3-methoxyphenyl)-N-(N''-methylcarbamoyl)formamidine | $C_{17}H_{19}N_3O_3$ | 313.3 | 138–40 | 65.2 / 65.2 | 6.1 / 6.2 | 13.4 / 13.6 | 15.3 / 15.4 | | |
| 27 | N,N'-Di-(3-methylphenyl)-N-(N''-methylcarbamoyl)-formamidine | $C_{17}H_{19}N_3O$ | 281.3 | 79–81 | 72.7 / 72.6 | 6.8 / 6.8 | 14.9 / 14.9 | | | |
| 28 | N,N'-Di-(3-chloro-4-methoxyphenyl)-N-(N''-methylcarbamoyl)formamidine | $C_{17}H_{17}Cl_2N_3O_3$ | 382.2 | 154–56 | 53.4 / 53.8 | 4.5 / 4.6 | 11.9 / 10.0 | 18.6 / 18.3 | | |

M.P.: 94°–95°

Analysis: $C_{16}H_{14}F_3N_3O$: Calc.: C, 59.9%; H, 4.4%; N, 13.1%; F, 17.3%. Found: C, 60.7%; H, 4.5%; N, 13.2%; F, 16.3%.

STARTING MATERIALS

The production of starting materials of formula IIb may be effected in accordance with Example 34 to 48:

EXAMPLE 34

N,N'-Di-(3-chlorophenyl)formamidine 225 g (2 mols) of 3-chloroaniline and 148.2 g (1 mol) of ortho-formic acid triethyl ester are heated in a distillation apparatus up to 100°–150° and the resulting ethyl alcohol is slowly separated by distillation over a Vigreux column. The resulting crude diarylformamidine is recrystallized from ethyl acetate.

M.P.: 113°–114°.

Analysis: $C_{13}H_{10}Cl_2N_2$: Molecular weight: 265.2: Calc.: N, 10.5%; Cl, 26.7%. Found: N, 10.5%; Cl, 26.5%.

The compounds of formula IIb of the following Examples 35 to 47 are produced in analogous manner to that described in Example 34.

EXAMPLE 49

N-Phenyl-N'-(3,4-dimethylphenyl)formamidine

M.P.: 112°–113°

Analysis: $C_{15}H_{16}N_2$: Molecular weight: 224.3: Calc.: C, 80.3%; H, 7.2%; N, 12.5%. Found: C, 80.2%; H, 7.0%; N, 12.7%.

EXAMPLE 50

N-Phenyl-N'-(3-trifluoromethylphenyl)formamidine

M.P.: 112°

Analysis: $C_{14}H_{11}F_3N_2$: Molecular weight: 264.3: Calc.: N, 10.2%; F, 21.6%. Found: N, 10.6%; F, 21.4%.

EXAMPLE 51

(N-Phenyl-N'-(3,4-dichlorophenyl)formamidine

M.P.: 135°

Analysis: $C_{13}H_{10}Cl_2N_{Cl}$, 26.8%. Molecular weight: 265.1: Calc.: N, 10.6%; Cl, 26.8%. Found: N, 10.6%; Cl, 26.6%.

EXAMPLE 52

(N-Phenyl-N'-(4-methylphenyl)formamidine

| Example | $R_4$ | $R_3$ | Empirical formula | Molecular weight | M.P. 0°C | ANALYSIS % Calc. / Found | | | | |
|---|---|---|---|---|---|---|---|---|---|---|
| | | | | | | C | H | N | Cl | Br |
| 35 | H | Br | $C_{13}H_{10}Br_2N_2$ | 354.1 | 186–88 | 44.1 | 2.8 | 7.9 | | 45.2 |
| | | | | | | 44.3 | 3.1 | 7.8 | | 45.0 |
| 36 | $CH_3$ | $CH_3$ | $C_{17}H_{20}N_2$ | 286.2 | 134–35 | 80.9 | 8.0 | 11.1 | | |
| | | | | | | 80.7 | 8.1 | 10.9 | | |
| 37 | H | Cl | $C_{13}H_{10}Cl_2N_2$ | 265.2 | 185 | 58.9 | 3.8 | 10.5 | 26.7 | |
| | | | | | | 58.8 | 3.9 | 10.7 | 27.1 | |
| 38 | H | $OCH_3$ | $C_{15}H_{16}N_2O_2$ | 256.3 | 117–18 | 70.2 | 6.3 | 10.9 | | |
| | | | | | | 70.2 | 6.2 | 10.9 | | |
| 39 | H | $SO_2N(CH_3)_2$ | $C_{17}H_{22}N_4O_4S_2$ | 410.5 | 229–30 | 49.7 | 5.4 | 13.7 | | |
| | | | | | | 49.5 | 5.3 | 13.7 | | |
| 40 | H | $CH_3$ | $C_{15}H_{16}N_2$ | 224.3 | 140–41 | 80.4 | 7.2 | 12.5 | | |
| | | | | | | 80.3 | 7.2 | 12.4 | | |
| 41 | Cl | $CH_3$ | $C_{15}H_{14}Cl_2N_2$ | 293.2 | 157–58 | 61.5 | 4.8 | 9.6 | 24.1 | |
| | | | | | | 61.7 | 4.8 | 9.5 | 24.3 | |
| 42 | Cl | Cl | $C_{13}H_{18}Cl_4N_2$ | 334.0 | 158–59 | 46.8 | 2.4 | 8.4 | 42.4 | |
| | | | | | | 46.8 | 2.5 | 8.3 | 41.6 | |
| 43 | $CH_3$ | H | $C_{15}H_{16}N_2$ | 224.3 | 123–25 | 80.4 | 7.2 | 12.5 | | |
| | | | | | | 80.2 | 7.1 | 12.3 | | |
| 44 | $OCH_3$ | H | $C_{15}H_{16}N_2O_2$ | 256.3 | 109 | 70.3 | 6.3 | 10.9 | | |
| | | | | | | 70.6 | 6.5 | 10.9 | | |
| 45 | Br | H | $C_{13}H_{10}Br_2N_2$ | 354.1 | 126–27 | 44.1 | 2.8 | 7.9 | | 45.2 |
| | | | | | | 44.7 | 2.8 | 7.9 | | 44.2 |
| 46 | Cl | $OCH_3$ | $C_{15}H_{14}Cl_2N_2O_2$ | 325.2 | 170–71 | 55.4 | 4.3 | 8.6 | 21.8 | |
| | | | | | | 55.5 | 4.5 | 9.0 | 22.3 | |
| 47 | $CF_3$ | H | $C_{15}H_{10}F_6N_2$ | 332.3 | 121–23 | 54.2 | 3.0 | 8.4 | | |
| | | | | | | 54.2 | 3.3 | 8.8 | | |

EXAMPLE 48

N-Phenyl-N'-(chlorophenyl)formamidine

A mixture of 25.5 g (0.2 mol) of 4-chloroaniline and 29.8 g (0.2 mol) of ethyl-N-phenylformimidate is heated in a distillation apparatus up to 100° over the course of 3 hours and the resulting ethyl alcohol is separated by distillation over a Vigreux column and under slightly reduced pressure (200 torr). The curde diarylformamidine is recrystallized from isopropanol.

M.P.: 123°–124°.

Analysis: $C_{13}H_{11}ClN_2$: Molecular weight: 230.7:

Calc.: C, 67.6%; H, 4.8%; N, 12.1%; Cl, 15.4%. Found: C, 67.8%; H, 4.7%; N, 12.5%; Cl, 15.0%.

The following starting materials of formula IIb are produced in analogous manner to that described in Example 48.

M.P.: 95°–97°

Analysis: $C_{14}H_{14}N_2$: Molecular weight: 210.3: Calc.: C, 79.8%; H, 6.7%; N, 13.3%. Found: C, 80.0%; H, 6.8%; N, 13.3%.

What is claimed is:

1. A compound of the formula:

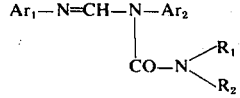

wherein $R_1$ is hydrogen or alkyl of 1 to 4 carbon atoms,
$R_2$ is alkyl of 1 to 4 carbon atoms, and either
$Ar_1$ and $Ar_2$ are the same, and are each phenyl or a substituted phenyl group selected from

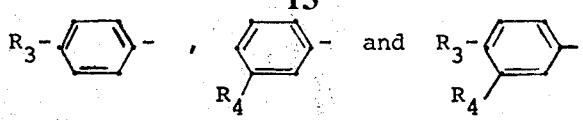

wherein
R$_3$ is chlorine, bromine, methyl or methoxy, and
R$_4$ is chlorine, bromine, methyl, methoxy or trifluoromethyl, or
Ar$_2$ is phenyl and
Ar$_1$ is a substituted phenyl group selected from

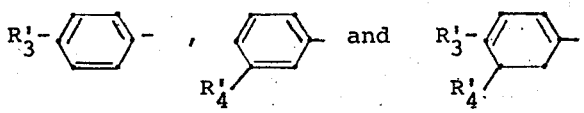

wherein
R$_3$' is chlorine or methyl and
R$_4$' is chlorine, methyl or trifluoromethyl,
with the proviso that Ar$_1$ and Ar$_2$ are other than

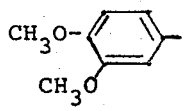

2. A compound of claim 1, wherein R$_1$ is hydrogen.
3. The compound of claim 2, which is N,N'-diphenyl-N-(N''-methylcarbamoyl)formamidine.
4. The compound of claim 2, which is N,N'-di-(3-bromophenyl)-N-(N''-methylcarbamoyl)formamidine.
5. The compound of claim 2, which is N,N'-di-(3-trifluoromethylphenyl)-N-(N''-methylcarbamoyl)formamidine.
6. The compound of claim 2, which is N,N'-(4-bromophenyl)-N-(N''-methylcarbamoyl)formamidine.
7. The compound of claim 2, which is N,N'-di-(3-chloro-4-methylphenyl)-N-(N''-methylcarbamoyl)formamidine.
8. The compound of claim 2, which is N,N'-di-(3-chlorophenyl)-N-(N''-methylcarbamoyl)formamidine.
9. The compound of claim 2, which is N,N'-di-(4-methylphenyl)-N-(N''-methylcarbamoyl)formamidine.
10. The compound of claim 2, which is N,N'-di-(3-methoxyphenyl)-N-(N''-methylcarbamoyl)formamidine.
11. The compound of claim 2, which is N,N'-di-(3-methylphenyl)-N-(N''-methylcarbamoyl)formamidine.
12. The compound of claim 2, which is N,N'-di-(3-chloro-4-methoxyphenyl)-N-(N''-methylcarbamoyl)formamidine.
13. The compound of claim 2, which is N-phenyl-N-(N''-methylcarbamoyl)-N'-(4-methylphenyl)formamidine.
14. The compound of claim 2, which is N-phenyl-N-(N''-methylcarbamoyl)-N'-(4-chlorophenyl)formamidine.
15. The compound of claim 2, which is N-phenyl-N-(N''-methylcarbamoyl)-N'-(3,4-dimethylphenyl)formamidine.
16. The compound of claim 2, which is N-phenyl-N-(N''-methylcarbamoyl)-N'-(3,4-dichlorophenyl)formamidine.
17. The compound of claim 2, which is N-phenyl-N-(N''-methylcarbamoyl)-N'-(3-trifluoromethylphenyl)formamidine.
18. A compound of claim 2, wherein R$_2$ is methyl and Ar$_1$ and Ar$_2$ are the same and are each a substituted phenyl group selected from

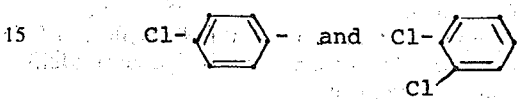

19. The compound of claim 18, which is N,N'-di-(4-chlorophenyl)-N-(N''-methylcarbamoyl)formamidine.
20. The compound of claim 18, which is N,N'-di-(3-dichlorophenyl)-N-(N''-methylcarbamoyl)formamidine.
21. A compound of claim 1, wherein R$_1$ and R$_2$ are each methyl and Ar$_1$ and Ar$_2$ are the same and are each a substituted phenyl group selected from

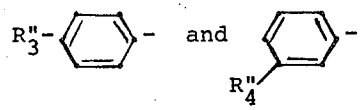

wherein R$_3$'' and R$_4$'' are each chlorine, bromine or methyl.
22. The compound of claim 21, which is N,N'-di-(4-bromophenyl)-N-(N''-dimethylcarbamoyl)formamidine.
23. The compound of claim 21, which is N,N'-di-(3-chlorophenyl)-N-(N''-dimethylcarbamoyl)formamidine.
24. The compound of claim 21, which is N,N'-di-(4-chlorophenyl)-N-(N''-dimethylcarbamoyl)formamidine.
25. The compound of claim 21, which is N,N-di-(4-methylphenyl)-N-(N''-dimethylcarbamoyl)formamidine.
26. The compound of claim 21, which is N,N'-di-(3-methylphenyl)-N-(N''-dimethylcarbamoyl)formamidine.
27. A compound of claim 1, wherein R$_1$ is alkyl of 1 to 4 carbon atoms and Ar$_1$ and Ar$_2$ are the same and are each phenyl or a substituted phenyl group selected from

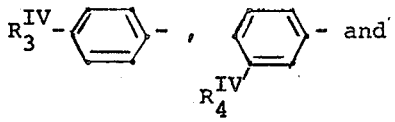

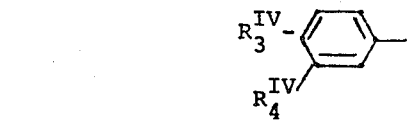

wherein R$_3^{IV}$ is chlorine or methoxy and R$_4^{IV}$ is chlorine, methoxy or trifluoromethyl.

28. The compound of claim 27, which is N,N'-diphenyl-N-(N''-methylcarbamoyl)formamidine.

29. The compound of claim 27, which is N,N'-di-(3,4-dichlorophenyl)-N-(N''-dimethylcarbamoyl)formamidine.

30. The compound of claim 27, which is N,N'-di-(4-methylphenyl)-N-(N''-dimethylcarbamoyl)formamidine.

31. The compound of claim 27, which is N,N'-di-(3-methoxyphenyl)-N-(N''-dimethylcarbamoyl)formamidine.

32. The compound of claim 27, which is N,N'-di-(3-chloro-4-methoxyphenyl)-N-(N''-dimethylcarbamoyl)formamidine.

33. A compound of claim 1, wherein $R_1$ is alkyl of 1 to 4 carbon atoms, $Ar_2$ is phenyl and $Ar_1$ is a substituted phenyl group selected from

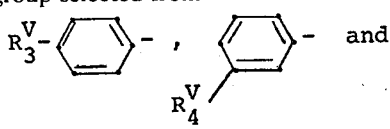

and

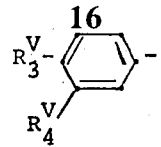

wherein $R_3^V$ is chlorine or methyl and $R_4^V$ is chlorine or methyl.

34. The compound of claim 33, which is N-phenyl-N-(N''-dimethylcarbamoyl)-N'-(3,4-dichlorophenyl)formamidine.

35. The compound of claim 33, which is N-phenyl-N-(N''-dimethylcarbamoyl)-N'-(3,4-dimethylphenyl)formamidine.

36. The compound of claim 33, which is N-phenyl-N-(N''-dimethylcarbamoyl)-N'-(4-chlorophenyl)formamidine.

37. The compound of claim 33, which is N-phenyl-N-(N''-dimethylcarbamoyl)-N'-(4-methylphenyl)formamidine.

* * * * *